(12) United States Patent
Tran

(10) Patent No.: US 6,482,218 B1
(45) Date of Patent: Nov. 19, 2002

(54) WIRE-SHAPED ULTRASONIC CATHETER WITH DIAMOND COATED HEAD FOR ULTRASONIC ANGIOPLASTY

(76) Inventor: Khanh Vien Tran, 32, chemin des Bourdons, F-93220 Gagny (FR)

( * ) Notice: Subject to any disclaimer, the term of this patent is extended or adjusted under 35 U.S.C. 154(b) by 0 days.

(21) Appl. No.: 09/177,475

(22) Filed: Oct. 23, 1998

(51) Int. Cl.7 .............................................. A61B 17/22
(52) U.S. Cl. ...................... 606/169; 606/171
(58) Field of Search .................... 606/1, 159, 169, 606/170, 171; 604/22

(56) References Cited

U.S. PATENT DOCUMENTS

| | | | |
|---|---|---|---|
| 3,433,226 A | * 3/1969 | Boyd | |
| 4,870,953 A | * 10/1989 | DonMichael et al. | |
| 5,163,421 A | * 11/1992 | Bernstein et al. | 606/159 |
| 5,209,719 A | * 5/1993 | Baruch et al. | |
| 5,217,474 A | * 6/1993 | Zacca et al. | 606/159 |
| 5,234,451 A | * 8/1993 | Osypka | 606/159 |
| 5,304,115 A | * 4/1994 | Pflueger et al. | 604/22 |
| 5,312,328 A | * 5/1994 | Nita et al. | 604/22 |
| 5,368,558 A | * 11/1994 | Nita | 604/22 |
| 5,380,273 A | * 1/1995 | Dubrul et al. | 604/22 |
| 5,397,293 A | * 3/1995 | Alliger et al. | 601/2 |
| 5,427,118 A | * 6/1995 | Nita et al. | 128/772 |
| 5,628,761 A | * 5/1997 | Rizik | 606/170 |
| 5,725,494 A | * 3/1998 | Brisken | 604/22 |

FOREIGN PATENT DOCUMENTS

| | | |
|---|---|---|
| DE | 39 36 162 | 6/1991 |
| DE | 40 36 570 | 5/1992 |
| WO | WO 92/11815 | * 7/1992 |
| WO | WO 92 11815 | 8/1992 |
| WO | WO 93 21835 | 11/1993 |

* cited by examiner

*Primary Examiner*—Ralph A. Lewis
(74) *Attorney, Agent, or Firm*—Schnader Harrison Segal & Lewis LLP

(57) ABSTRACT

The present invention pertains to a wire-shaped ultrasonic catheter for ultrasonic angioplasty. The ultrasonic catheter head is provided with a diamond coating. The catheter has a cylindrical sonotrode and a thin ultrasound catheter which together form a resonant system. The catheter is made from a thin stainless steel ultrasound waveguide. The catheter is coupled to a mechanical connection system at one end and at the other end to a hardened, bulb-shaped stainless steel catheter tip having a cylindrical, spherical or rounded conical shape with a diamond powder coating.

6 Claims, 2 Drawing Sheets

WIRE-SHAPED ULTRASONIC CATHETER WITH DIAMOND COATED HEAD FOR ULTRASONIC ANGIOPLASTY

FIELD OF THE INVENTION

The present invention is a filiform ultrasound catheter, in stainless steel, whose distal end is formed by a bulb-shaped catheter tip, that is substantially spherical, coated with a diamond coating.

BACKGROUND ART

The objective of conventional angioplasty procedures using balloon catheters for dilation, is to restore the lumen of arteries that are partially obstructed or occluded by blood clots and/or atheroma. For this purpose, vascular surgeons and intervention radiologists pass a balloon catheter through the residual arterial lumen, inflate the balloon to flatten the atheroma against the arterial wall, which enables blood circulation to be restored. A stent may then be inserted to reduce the risk of recurrent stenosis.

If the said balloon catheter cannot be passed through the said stenosis: either because the diameter of the said residual arterial lumen is too narrow; or because there is total occlusion; or because there are calcified plaques of atheroma; or because stenosis is multiple, the sole remaining solution is a bypass procedure to replace the damaged segment of the atheromatous artery with a natural or artificial prosthesis. Bypass procedure entails a heavy, traumatizing operation with risks related to heavy surgery that it is preferable to avoid whenever possible.

Precisely, ultrasound transluminal angioplasty systems, due to the effect of ultrasound on atheroma, restore the possibility of conducting conventional angioplasty by widening the said diameter of the residual arterial lumen or by tunneling through the stenosis.

Alternatively, reamers can be used for angioplasty. These systems using diamond-tipped reamers rotating around a metal guide have very high rotating speeds. For this reason, and due to their inertia, when their movement is set in motion these said diamond-tipped reamers draw the metal guide towards pathways of non-zero radius around the guide before stabilizing themselves in normal operating position to attack the stenosis. Deprived of guidance, the pathway of these rotating reamers is no longer controlled, and this excursive tendency to move over wider pathways is even further accentuated. It is during these excursions that the diamond-tipped reamers carry the danger of injuring the arterial wall in particular in arteries of narrow diameter. Ultrasound catheters, on the other hand, since they operate by longitudinal vibration in relation to the metal guide, are not subject to this tendency to follow a pathway away from the guide and to damage the arterial wall. These ultrasound catheters offer better security for the arterial wall.

The present invention brings the following advantages:

1) Compared with conventional filiform ultrasound catheters, whose catheter tip does not have a diamond coating, it is more effective in attacking the calcified, hardened plaques of atheroma without reducing its efficacy in breaking up other biological tissues.

2) The size of the diamond grains set in the diamond coating is such that very small debris is produced which can be easily removed by aspiration or through natural routes.

3) Compared with angioplasty systems using rotating diamond-tipped reamers, it entails lesser risk of injuring the arterial wall.

SUMMARY OF THE INVENTION

The present invention pertains to a wire-shaped ultrasonic catheter for ultrasonic angioplasty. The ultrasonic catheter head is provided with a diamond coating. The catheter has a cylindrical sonotrode and a thin ultrasound catheter which together form a resonant system. The catheter is made from a thin stainless steel ultrasound waveguide. The catheter is coupled to a mechanical connection system at one end and at the other end to a hardened, bulb-shaped stainless steel catheter tip having a cylindrical, spherical or rounded conical shape with a diamond powder coating.

DETAILED DESCRIPTION OF THE DRAWINGS

The analysis given below of the functioning of ultrasound angioplasties will help to understand the qualities of the present invention in breaking up plaques of calcified atheroma.

a) Description of an Ultrasound Angioplasty Unit and its Functioning.

Figure 1:
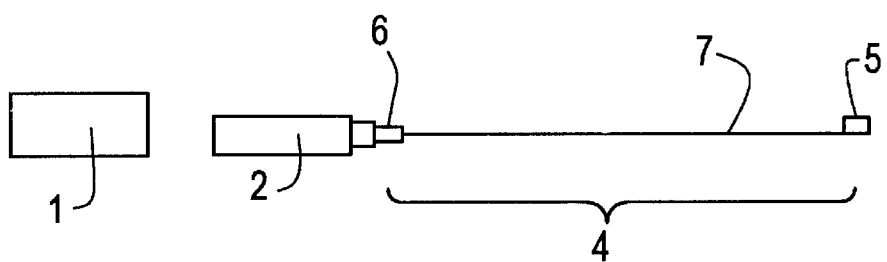
FIG. 1 is a schematic view of a conventional ultrasound angioplasty unit.

FIG. 1 shows a standard ultrasound angioplasty unit comprising: 1) an electric generator (1) supplying an electromechanical transducer (2) which is connected via mechanical coupling (6) to a filiform, long, flexible ultrasound catheter (4) whose distal end is a bulb-shaped catheter tip (5) that is substantially spherical.

This complex unit is designed so that it may convey to the catheter tip (5) a longitudinal back and forth movement at ultrasound frequency, in other words longitudinal ultrasound vibrations.

The flexibility of the filiform catheter (4) means that is can be inserted into human arteries and is able to follow their curves so that the catheter tip (5) can be brought into contact with the stenoses of the occluded arteries. Subsequently the ultrasound energy transmitted by the catheter tip (5) enables a pathway to be pierced through the stenoses so that the occluded arteries can be re-opened.

Finally, an ultrasound angioplasty system, in transluminal ultrasound angioplasty procedure, must allow the insertion of an ultrasound transmitter, i.e. the catheter tip (5), into the occluded arteries so that it can be brought into contact with the stenoses in order to clear the stenoses with ultrasound energy. Also, because of the "long, flexible filiform shape" of the catheter (4) this transmitter is able to go wherever a balloon catheter can go. In particular, in the presence of obstructions which do not allow passage of the balloon catheter for dilation, the ultrasound catheter of the present invention should be able to open a passageway through these obstructions. This can then allow a balloon catheter to be used.

The shape of the transluminal ultrasound angioplasty catheter, made up of a waveguide that is filiform, long and flexible terminating at its distal end with a bulb-shaped catheter tip, was the subject of U.S. Pat. No. 3,433,226 to Boyd. However at lines 63, 64 . . . column 4, Boyd acknowledges that he had not fully understood the exact mechanisms under which the ultrasound catheter is able to achieve the observed destruction of calcified atheroma plaques.

As we have set out to improve its functioning, we feel it would be of interest to analyze the mechanisms of interaction between the ultrasounds transmitted by the catheter tip and the complex biological medium which forms the atheroma. This is the object of the following paragraphs.

b) Effects of Ultrasound on Atheroma

In a complex material medium formed by atheroma, the ultrasonic vibrations of the catheter tip (5) produces the following two important effects: 1) pneumatic drill effect on solid medium; and 2) cavitation in a liquid or semi-liquid medium.

I) Pneumatic Drill Effect on a Solid Medium

Figure 3:
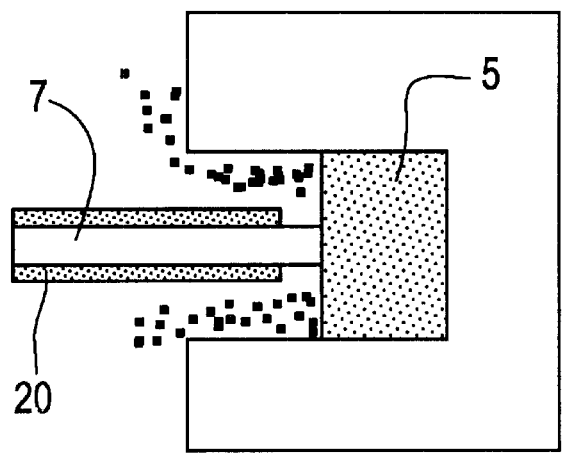
FIG. 3 is a cross-sectional view of an ultrasonic catheter showing the pneumatic drill effect on a solid medium.

When said catheter tip (5) is in contact with a solid medium, such as for example a calcified atheroma plaque, the longitudinal movement of the catheter tip (5) acts like a pneumatic drill on the atheroma plaque as is shown in FIG. 3. It is a Pneumatic drill effect but at ultrasound frequency. This effect ceases when the catheter tip (5) is no longer in contact with the calcified plaque. Its efficacy in breaking up solid calcified atheroma increases with a greater difference in hardness between catheter tip (5) and the calcified atheroma.

Hence there is an advantage in choosing a catheter tip (5) that is extremely hard. It is this area which must be explored to improve the efficacy of transluminal ultrasound angioplasty catheters for breaking up hard, calcified plaques of atheroma.

II) Cavitation in a Liquid or Semi-liquid Medium

Human blood or other biological tissues are strongly hydrated media.

Figure 4:
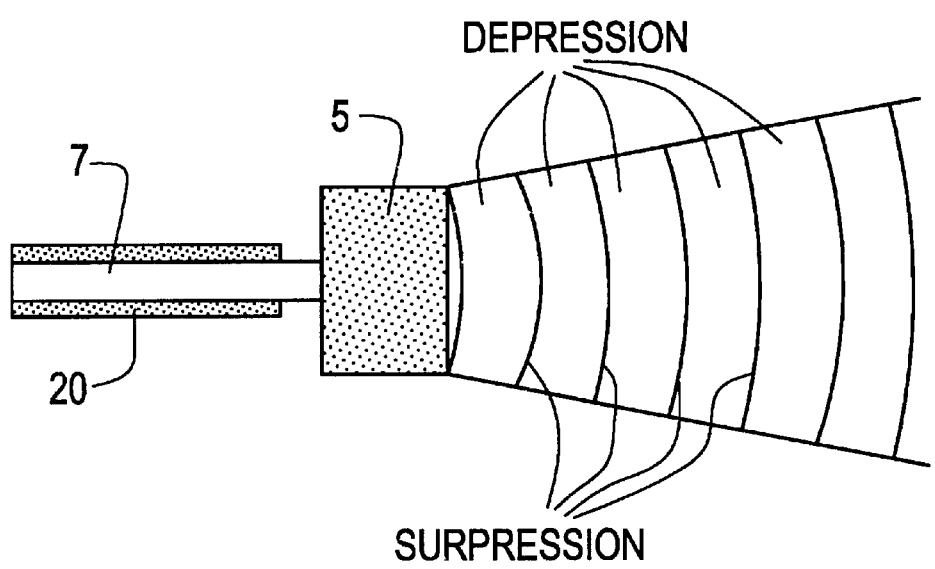
FIG. 4 is illustrative of the system of pressure waves set up by an ultrasonic catheter.

When the catheter tip (5) is inserted into a liquid medium and excited by high power ultrasound waves, it is the site of a high-powered ultrasonic vibration. In the liquid ahead of the catheter tip, a system of pressure waves is set up (FIG. 4) with zones of very high pressure (pressure antinodes) and zones of very low pressure (pressure nodes). This liquid is consequently subjected to strong pressure variations and therefore becomes the site of strong turbulence whose strength is related to the intensity of the ultrasound waves. Above a certain limit, the phenomenon of CAVITATION occurs. This phenomenon of cavitation, which in particular causes the breaking up of cell walls, lobules etc. in biological tissues, only acts on the non-calcified parts of the atheroma plaques and is totally ineffective against hard, calcified atheroma plaques which do not respond to pressure variations in surrounding liquids.

Cavitation is:
I) related to the frequency and magnitude of ultrasound vibrations emitted by the catheter tip,
  ii) related to the characteristics of the biological media concerned,
  iii) unrelated to the type of material forming the catheter tip.

Therefore when an excited ultrasound catheter tip (5) is in contact with a site of stenosis, the following effects can be expected:
  I) If, ahead of catheter tip (5) there are biological tissues which do not comprise calcified plaques, then catheter tip (5) will pierce a tunnel through the latter under the phenomenon of cavitation which causes the walls of the various cells to break up. The debris formed is then ejected and dispersed in all directions by the turbulence created by the ultrasound vibrations agitating this liquid medium.
  ii) If catheter tip (5) comes up against a solid calcified atheroma plaque, their interaction is governed by the pneumatic drill effect. Under this effect the solid matter which forms the plaques can be pulverized.

In reality, as all the above takes place in a liquid medium, and as the contact between catheter tip (5) and said plaque is not permanent, it is easy to understand that cavitation takes place as soon as there is no contact, but stops when contact is again made. In particular, cavitation produces the ejection of mineral and biological debris torn away by the pneumatic drill effect.

Moreover, since that solid debris is then subjected to a liquid medium that is highly agitated by the ultrasound waves, the debris is given projectile force and will therefore assist in tunneling through the obstruction.

Such are the physical mechanisms at work during re-opening of the lumen using the ultrasound angioplasty technique for an occluded artery.

Usually, owing to the resonance functioning of ultrasound catheters used in procedures, authors only mention cavitation and are often unaware of the pneumatic drill effect. Yet, in the presence of hard, calcified plaques of atheroma, cavitation is unable to cause their destruction as they are insensitive to pressure variations in the surrounding liquid medium.

The ultrasound angioplasty technique contributes to widening atheromatous arteries. Experience has shown in particular that it is the hard, calcified plaques of atheroma which raise problems for the different transluminal angioplasty techniques, especially in ultrasound transluminal angioplasty.

In the light of the above, it can be seen that an improvement in the efficacy of ultrasound angioplasty catheters can be achieved by giving priority to: a) either the Cavitation effect; b) or the Pneumatic drill effect; c) or the Cavitation and the Pneumatic drill effect.

Along the same lines of reasoning, it can be seen that an improvement in the Cavitation phenomenon can be obtained by varying ultrasound parameters such as ultrasound frequency and magnitude, the type of filiform ultrasound waveguide, and the contact between said filiform wave guide and the surrounding liquid medium. The type of metal of which the catheter tip is made is of no consequence here since all metals are harder than water.

An improvement in the Pneumatic drill effect can be obtained by improving not only ultrasound and contact parameters, but also and fundamentally by improving the density and hardness of the material forming the catheter tip. If it is less hard than solid, the tip will flatten on contact with the solid instead of pulverizing it.

To conclude, improving the efficacy of the catheter in attacking the plaques of atheroma, whether calcified or not, requires increased ultrasound magnitude, decreased friction between the filiform ultrasound waveguide and the surrounding biological medium, and increased density and hardness of the material forming the catheter tip.

However, in practice, the above conclusions must also give consideration to the physics of the materials. Our analysis of the physical dimensions involved gives the following figures:
  a) the effective ultrasound frequency band ranges from 10,000 Hz to 100,000 Hz,
  b) cavitation is produced with magnitudes of over a few tenths of a micrometer,
  c) with ultrasound elongations higher than 300 or 400 micrometers, the limits of elasticity of most metals and known alloys are exceeded, and d) experience has shown that plaques of calcified atheroma have a very wide range of degrees of hardness, ranging from very brittle plaques to plaques of extreme hardness comparable to that of stones, gravel, and even harder.

It must be remembered that if the flexible, filiform ultrasound catheter operates outside its limits of elasticity, non-linear phenomena occur initially producing very swift overheating followed by rupture which is very serious and undesirable. Therefore reason has it that ultrasound catheters must be used below their metal yield points. We estimate that the ultrasound vibrations of magnitudes in the region of 100 micrometers are reasonable values to obtain good cavitation phenomena without running the risk of causing catheter breakage. These vibration magnitudes can be easily obtained with materials such as stainless steel and other metal alloys that are less "exotic" than titanium or aluminum alloys, and are considered to be good and very good ultrasound conductors with elastic and superelastic properties. In this case, stainless steel competes well with these "exotic" alloys and metals.

Previous attempts have been made to improve the functioning of flexible, filiform ultrasound catheters with a bulb-shaped tip.

In particular the improvements brought by U.S. Pat. No. 5,304,115 to Pflueger are cited which relate to the ultrasound parameters of the catheter, using the above-mentioned "exotic" materials, and the ultrasound catheter tip made in the same materials as the filiform, ultrasound waveguide specifying the possible shapes of this tip, structural details, and surface treatments and other coatings to obtain superficial hardening of these titanium-based alloys.

It appears that the choice of these titanium-based alloys is a good choice to improve the ultrasound qualities of the assembly and therefore for cavitation-related phenomena.

However, as titanium and its alloys are light metals and do not have very high intrinsic hard properties, this choice does not improve the pneumatic drill effect of the catheter tip. This is recognized in Pflueger, where it is suggested to improve the hardness of the catheter tip by different surface treatments described in other parts of the patent.

These surface treatments are complicated, and costly and do not yield hardness that is equivalent to that of alumina-based ceramics or diamond coatings. Only these coatings are able to pulverize the hardest plaques of calcified atheroma.

In accordance with the present invention, improvement can easily be achieved with flexible, filiform ultrasound catheters in stainless steel having a catheter tip (5) that is bulb-shaped and coated with a diamond coating (10).

The hardness of diamond coatings is well suited for breaking up hard materials since these coatings are used for oil drilling and for dental drills etc. Also, since these coatings are deposited in thin layers on the catheter tips (5) they cause little or no disturbance to ultrasound response. The size of the encrusted diamond grains means that the debris obtained after breaking up the solid calcified atheroma plaques is solid debris of very small diameter which can be easily removed by aspiration or by natural routes. Finally the density of stainless steel assists the pneumatic drill effect.

To summarize, for ultrasound angioplasty, ultrasound catheters (4) in stainless steel fitted with a catheter tip (5) coated with a diamond coating (10) as described in the present invention can achieve increased efficacy in breaking up calcified plaques of atheroma without losing their effectiveness in breaking up non-calcified atheroma, the production of solid debris of very small diameter which can be easily removed by aspiration or by natural routes, and improved security for the arterial wall due to their operating mode in longitudinal vibrations in relation to the metal guide. They are not subject to the tendency to veer towards the arterial wall and injure the latter as is the case with rotating diamond-tipped reamers.

Figure 2:
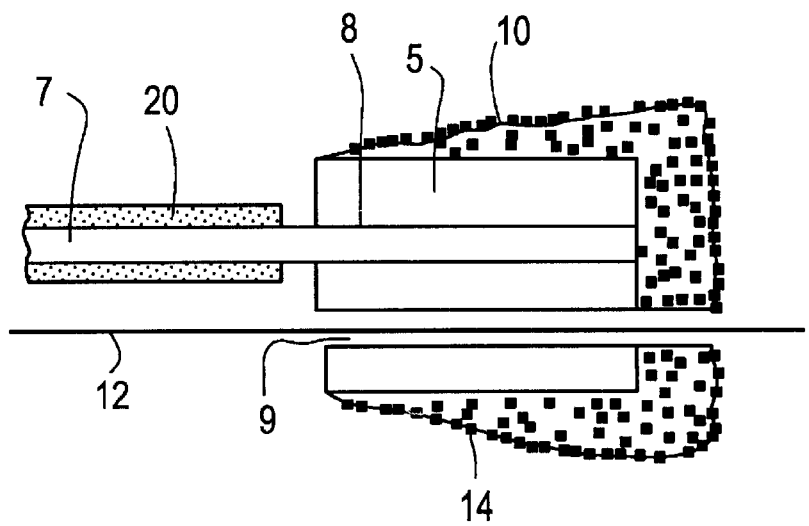
FIG. 2 is a cross-sectional view of the catheter of the present invention.

In one embodiment of the ultrasound angioplasty unit shown in FIG. 1, the electromechanical transducer (2) is a cylindrical sonotrode made in a metal that is a good ultrasound conductor. FIG. 2 shows an embodiment of the filiform, flexible ultrasound catheter (4) made up of a filiform ultrasound waveguide (7) coupled at its distal end to a catheter tip (5) that is bulb-shaped and substantially round, coated with a thin layer (10) of diamond coating.

The ultrasound waveguide (7) is a metal, elastic or superelastic wire, of uniform diameter ranging from 0.4 mm to 0.9 mm with a total length between 0.1 m and 1.5 m. The catheter tip (5), coated with a thin layer (10) of diamond coating, is a metal cylinder whose distal end may be cylindrical, spherical or a round conical shape, its length being at least 0.5 mm and its diameter being greater than 1 mm. It is pierced by a first longitudinal hole (9) having a diameter of 0.4 mm to 0.6 mm to give passageway to the metal guide (12) or to the X-ray opacifying liquid, and by a second longitudinal hole (8) whose inner diameter must allow assembly with the ultrasound waveguide (7) by brazing, gluing or embedding according to the type of materials forming the catheter tip (5) and the ultrasound waveguide (7).

The diamond grains (14) of the thin diamond coating layer (10) have a diameter of between 10 microns and 100 microns.

The size of the sonotrode (7) and the filiform ultrasound waveguide (7) is such that the system formed by the sonotrode (7) and the filiform ultrasound catheter (4) forms a resonant system.

In a preferred embodiment, the ultrasound waveguide (7) and the catheter tip (5) are in brazable stainless steel, of medical quality and are mounted by brazing, using a brazing solder of low-temperature silver type. During assembly by brazing, the temperature reached by these two parts must not cause their weakening.

In another embodiment, the catheter tip (5) may be made in a hard ceramic, or a ceramic containing diamond powder, or in hard ceramic containing alumina or alumina compounds.

In a further embodiment, the ultrasound waveguide (7) is a titanium or titanium alloy wire that is super elastic. In this case, the assembly of the ultrasound waveguide (7) and the catheter tip (5) is made by setting or gluing.

To improve the functioning of the catheter, it is advantageous to reduce catheter/blood coupling by coating the ultrasound waveguide with an anti-friction coating (20) such as Teflon or biocompatible matters having the same anti-friction property.

What is claimed is:

1. A device for ultrasound angioplasty, comprising:
    a cylindrical sonotrode;
    a thin ultrasound catheter forming a resonant system with said sonotrode and having a proximal end and a distal end, and made from a thin stainless steel ultrasound waveguide coupled:
        at the proximal end to a said sonotrade and
        at the distal end to a hardened bulb-shaped catheter tip whose distal end is of a shape selected from the group consisting of cylindrical, spherical and rounded conical, and is coated with a layer of diamond powder, wherein said catheter tip is made from ceramic material and has the following measurements: length of at least 0.5 mm and outer diameter of at least 1 mm.

2. A device for ultrasound angioplasty, comprising:

a cylindrical sonotrode;

a thin ultrasound catheter forming a resonant system with said sonotrode and having a proximal end and a distal end, and made from a thin stainless steel ultrasound waveguide coupled:
 at the proximal end to a said sonotrade and
 at the distal end to a hardened bulb-shaped catheter tip whose distal end is of a shape selected from the group consisting of cylindrical, spherical and rounded conical, wherein said catheter tip is coated with ceramic material containing diamond powder and has the following measurements: length of at least 0.5 mm and outer diameter of at least 1 mm.

3. A device for ultrasound angioplasty, comprising:

a cylindrical sonotrode;

a thin ultrasound catheter forming a resonant system with said sonotrode and having a proximal end and a distal end, and made from a thin stainless steel ultrasound waveguide coupled:
 at the proximal end to a said sonotrade and
 at the distal end to a hardened bulb-shaped catheter tip whose distal end is of a shape selected from the group consisting of cylindrical, spherical and rounded conical, wherein said catheter tip is coated with ceramic containing alumina compounds and has the following measurements: length of at least 0.5 mm and outer diameter of at least 1 mm.

4. A device for ultrasound angioplasty, comprising:

a cylindrical sonotrode;

a thin ultrasound catheter forming a resonant system with said sonotrode and having a proximal end and a distal end, and made from a thin stainless steel ultrasound waveguide coupled:
 at the proximal end to a the sonotrode, and
 at the distal end to a hardened bulb-shaped stainless steel catheter tip whose distal end is of a shape selected from the group consisting of cylindrical, spherical and rounded conical, and is coated with a layer of diamond powder, wherein said catheter tip is a brazable stainless steel cylinder whose length is greater that 0.5 mm, whose outer diameter is greater than 1 mm, and which is pierced with an axial hole and the inner diameter of said hole is assembled to the ultrasound waveguide by a step selected from the group consisting of brazing, embedding, welding and gluing, wherein the assembly of said thin ultrasound waveguide is made from brazable stainless steel with said catheter tip coated with a diamond coating made by brazing, using a brazing solder of low-temperature Silver brazing solder type.

5. A device for ultrasound angioplasty, comprising:

a cylindrical sonotrode;

a thin ultrasound catheter forming a resonant system with said sonotrode and having a proximal end and a distal end, and made from a thin stainless steel ultrasound waveguide coupled:
 at the proximal end to a the sonotrode and
 at the distal end to a hardened bulb-shaped stainless steel catheter tip whose distal end is of a shape selected from the group consisting of cylindrical, spherical and rounded conical, and is coated with a layer of diamond powder; and
 wherein the assembly of said thin ultrasound waveguide is made from brazable stainless steel with said catheter tip coated with a diamond coating made by brazing, using a brazing solder of low temperature Silver brazing solder type.

6. A device for ultrasound angioplasty, comprising:

a cylindrical sonotrode;

a thin ultrasound catheter forming a resonant system with said sonotrode and having a proximal end and a distal end, and made from a thin stainless steel ultrasound waveguide coupled:
 at the proximal end to a said sonotrode and
 at the distal end to a hardened bulb-shaped stainless steel catheter tip whose distal end is of a shape selected from the group consisting of cylindrical, spherical and rounded conical, and is coated with a layer of diamond powder;

wherein said thin ultrasound waveguide is made from a brazable stainless steel wire and has a uniform outer diameter of between 0.4 mm and 0.9 mm and a total length ranging from 100 mm to 1500 mm and is compatible with the resonance frequency of the resonant system formed by said sonotrode and said thin ultrasound catheter; and wherein the assembly of said thin ultrasound waveguide is made from brazable stainless steel with said catheter tip coated with a diamond coating made by brazing, using a brazing solder of low-temperature Silver brazing solder type.

* * * * *